(12) United States Patent
Ogusu (10) Patent No.: US 9,328,380 B2
(45) Date of Patent: May 3, 2016

(54) FLOW PASSAGE DEVICE AND TESTING SYSTEM USING THE SAME

(75) Inventor: Makoto Ogusu, Shimotsuke (JP)

(73) Assignee: Canon Kabushiki Kaisha, Tokyo (JP)

( * ) Notice: Subject to any disclaimer, the term of this patent is extended or adjusted under 35 U.S.C. 154(b) by 108 days.

(21) Appl. No.: 14/116,088

(22) PCT Filed: Apr. 23, 2012

(86) PCT No.: PCT/JP2012/061503
§ 371 (c)(1),
(2), (4) Date: Nov. 6, 2013

(87) PCT Pub. No.: WO2012/153667
PCT Pub. Date: Nov. 15, 2012

(65) Prior Publication Data
US 2014/0106984 A1   Apr. 17, 2014

(30) Foreign Application Priority Data

May 10, 2011   (JP) ................................. 2011-105635

(51) Int. Cl.
| | | |
|---|---|---|
| *C12Q 1/68* | (2006.01) | |
| *B01L 7/00* | (2006.01) | |
| *G01N 21/64* | (2006.01) | |
| *B01L 3/00* | (2006.01) | |
| *G01N 35/00* | (2006.01) | |

(52) U.S. Cl.
CPC ............... *C12Q 1/686* (2013.01); *B01L 3/5027* (2013.01); *B01L 7/52* (2013.01); *G01N 21/6428* (2013.01); *B01L 2300/0877* (2013.01); *B01L 2300/168* (2013.01); *B01L 2300/1827* (2013.01); *B01L 2300/1883* (2013.01); *G01N 2035/00158* (2013.01)

(58) Field of Classification Search
None
See application file for complete search history.

(56) References Cited

U.S. PATENT DOCUMENTS

| | | | |
|---|---|---|---|
| 2002/0109844 A1* | 8/2002 | Christel et al. | ................. 356/417 |
| 2003/0157503 A1 | 8/2003 | McGarry | |
| 2004/0227199 A1 | 11/2004 | Fukuyama | |
| 2005/0009101 A1* | 1/2005 | Blackburn | ...................... 435/7.1 |
| 2005/0255007 A1 | 11/2005 | Yamada | |
| 2006/0257069 A1* | 11/2006 | Sims | ..................... G02B 6/3538 385/16 |
| 2010/0216193 A1 | 8/2010 | Gomi | |
| 2011/0207137 A1* | 8/2011 | Malik | ....................... B01L 7/52 435/6.12 |
| 2012/0135511 A1* | 5/2012 | Battrell et al. | ............. 435/287.2 |

FOREIGN PATENT DOCUMENTS

| | | |
|---|---|---|
| JP | 2002-520621 A | 7/2002 |
| JP | 2003519363 A | 6/2003 |
| JP | 2003-215139 A | 7/2003 |

(Continued)

*Primary Examiner* — Jill Warden
*Assistant Examiner* — Timothy G Kingan
(74) *Attorney, Agent, or Firm* — Canon USA, Inc. IP Division (57) ABSTRACT

A real time analysis in accordance with temperature change and highly sensitive detection are permitted. A flow passage device has a flow passage (1) and is able to heat a fluid in the flow passage. A state of the fluid in the flow passage is observable using light. The flow passage device includes a first member (2) including an observation surface (3) and an upper inner wall surface (4), and a second member (5) including a lower inner wall surface that opposes the upper inner wall surface (4) and that is part of inner walls of the flow passage. A heating resistor (6) having a reflective surface that reflects light is provided on the lower inner wall surface. The light reflected by the reflective surface passes through the upper inner wall surface (4) and the observation surface (3).

12 Claims, 7 Drawing Sheets

(56) References Cited

FOREIGN PATENT DOCUMENTS

| | | | |
|---|---|---|---|
| JP | 2005-323519 | A | 11/2005 |
| JP | 2006090784 | A | 4/2006 |
| JP | 2006208139 | A | 8/2006 |
| JP | 2007-45012 | A | 2/2007 |
| JP | 2008-275333 | A | 11/2008 |
| JP | 2009-542207 | A | 12/2009 |
| WO | 2009/054473 | A1 | 4/2009 |
| WO | 2010/088514 | A1 | 8/2010 |

* cited by examiner

FLOW PASSAGE DEVICE AND TESTING SYSTEM USING THE SAME

TECHNICAL FIELD

The present invention relates to a flow passage device that has a flow passage and allows the state in the flow passage to be detected, and relates to a testing system using the flow passage device. In particular, the present invention relates to a flow passage device that allows fluorescence detection to be performed. The fluorescence detection is used in genetic tests, protein tests, and so forth.

BACKGROUND ART

In existing specimen tests, fluid reagents are required for chemical analyses, preparation of reagents, chemical syntheses, and reaction detection on the order of milliliters (ml) to microliters (μl). Tests performed using test-tubes or the like can now be performed on the order of nanoliters (nl) by formation of a fine flow passage (including a reaction field) using a litho-process and a thick film process technology. The micro total analysis system (μ-TAS) is a technology that utilizes such fine reaction fields. The μ-TAS technology is applicable to fields of genetic testing, chromosomal testing, cell testing and so forth used for medical tests and diagnoses, biotechnologies, tests of substances present in very small amounts in the environment, research on the cultivating environment for agricultural products and the like, genetic tests of agricultural products, and so forth. One example of use of a flow passage device, to which the μ-TAS technology is introduced, as a reaction field is the polymerase chain reaction (PCR).

In order to analyze a very small amount of nucleic acid such as deoxyribonucleic acid (DNA) or ribonucleic acid (RNA), the nucleic acid needs to be amplified to an amount at which the nucleic acid can be detected by fluorescence detection or other light detection. The PCR method has been used as a method of amplifying the nucleic acid.

PTL 1 discloses an optical analysis system as a system that uses the μ-TAS and performs the PCR as described above. The optical analysis system disclosed in PTL 1 includes a substrate including a microfluidic channel, a thermal generating unit operable to provide heat to and absorb heat from at least a portion of the microfluidic channel, and an image sensor disposed in relation to the substrate such that the portion of the channel is within the field of view of the image sensor.

One of the main problems to be solved in a flow passage device using a fine flow passage is to efficiently detect a light signal in the flow passage. In view of the above-described problem, PTL 2 discloses a technology in which inner surfaces of a flow passage are made to be reflective surfaces having high reflectivity by mirror finishing or another processing method so as to allow light emitted in the flow passage to be efficiently obtained.

CITATION LIST

Patent Literature

PTL 1 PCT Japanese Translation Patent Publication No. 2009-542207

PTL 2 Japanese Patent Laid-Open No. 2003-215139

SUMMARY OF INVENTION

Technical Problem

There has been a need for a flow passage device for light detection that allows the amount of light emitted in the flow passage device due to a temperature change to be detected in a highly sensitive and real time manner.

Although the structure disclosed in PTL 2 is considered to have an increased sensitivity in detection, there is no description about a heating unit. Thus, it is unlikely that the technology disclosed in PTL 2 is applied to a real time analysis such as detection of a change in the state of a fluid due to a temperature change in a PCR reaction, a thermal melting reaction, and so forth.

The present invention provides a flow passage device, with which highly sensitive detection and a real time analysis can be realized, and provides a testing system using this flow passage device.

Solution to Problem

In order to solve the above-described problem, according to an aspect of the present invention, a flow passage device has a flow passage and can heat a fluid in the flow passage. A state of the fluid in the flow passage is observable using light. The flow passage device includes an observation surface used to observe a state in the flow passage, a first inner wall surface that is part of inner walls of the flow passage, and a second inner wall surface that opposes the first inner wall surface and that is part of the inner walls of the flow passage. In the flow passage device, a heating resistor, which has a reflective surface that reflects light, is provided in the second inner wall surface.

According to another aspect of a present invention, a flow passage device has a flow passage and can heat a fluid in the flow passage. A state of the fluid in the flow passage is observable using light. The flow passage device includes a first member that includes an observation surface used to observe a state in the flow passage and an upper inner wall surface that is part of inner walls of the flow passage, and a second member that includes a lower inner wall surface that opposes the upper inner wall surface and that is part of the inner walls of the flow passage. In the flow passage device, a heating resistor, which has a reflective surface that reflects light, is provided in the second inner wall surface of the second member, and the light reflected by the reflective surface passes through the upper inner wall surface and the observation surface.

Advantageous Effects of Invention

According to the present invention, a heating resistor that heats a fluid provides a reflective surface. Thus, a highly sensitive real time analysis can be realized using a simple structure.

DESCRIPTION OF EMBODIMENTS

An embodiment according to the present invention will be described in detail below with reference to the drawings.

Figure 1A:
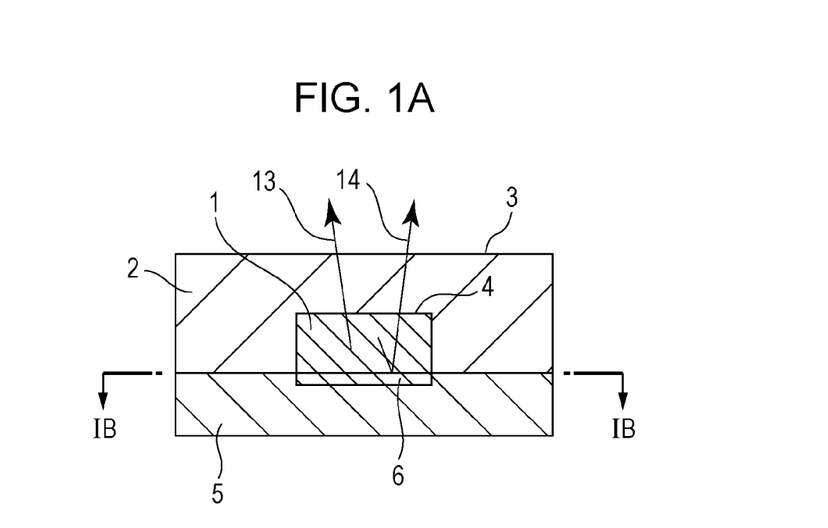
FIGS. 1A to 1D are schematic diagrams illustrating a flow passage device according to the present invention.
Figure 1B:
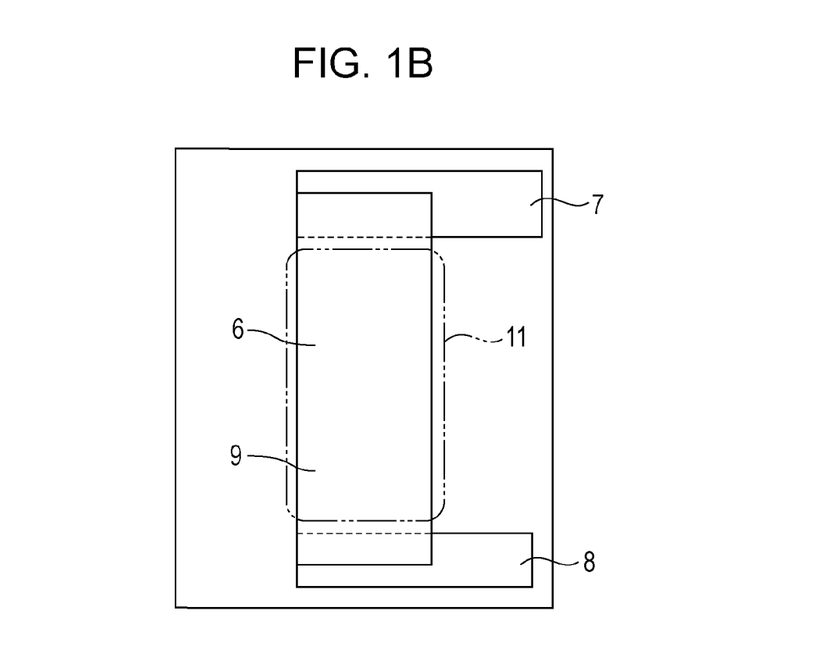
Figure 1C:
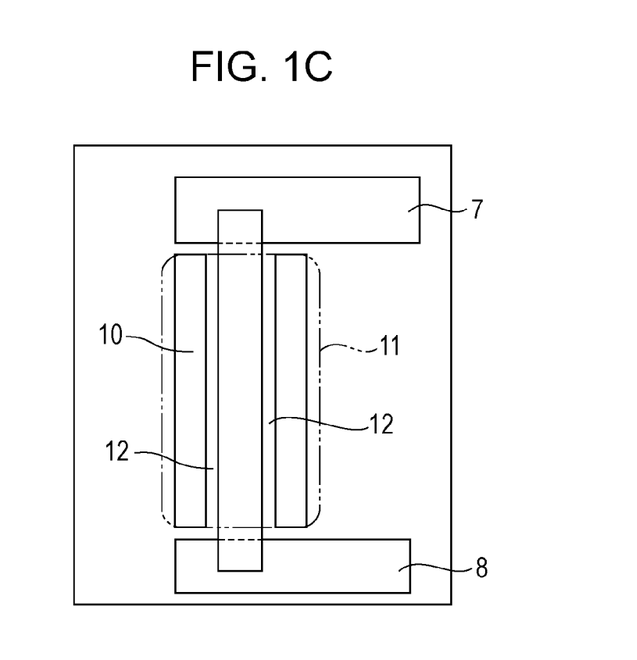
Figure 1D:
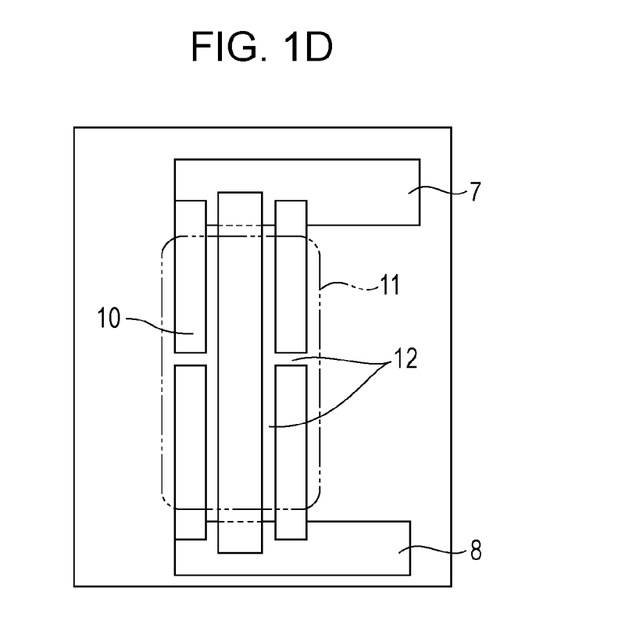

FIGS. 1A to 1D are schematic diagrams of a flow passage device according to the present invention. FIG. 1A is a sectional view taken along a direction in which a fluid flows in a flow passage. FIG. 1B is a top plan view of plane IB-IB' of the flow passage device in FIG. 1A. FIGS. 1C and 1D illustrate examples of modifications of the flow passage device illustrated in FIG. 1B.

As illustrated in FIGS. 1A to 1D, the flow passage device according to the present embodiment has a flow passage 1. A fluid in the flow passage 1 can be heated and the state of the fluid in the flow passage 1 can be optically detected, thereby being observed.

A first member 2 has an observation surface 3 and an upper inner wall surface 4. The observation surface 3 is provided to observe a state in the flow passage 1. The upper inner wall surface 4 serves as a first inner wall surface, which is part of inner walls of the flow passage 1. A second member 5 has a lower inner wall surface that opposes the upper inner wall surface 4 and serves as a second inner wall surface, which is part of the inner walls of the flow passage 1.

A heating resistor 6 having a reflective surface that reflects light is formed on the lower inner wall surface of the second member 5. That is, an upper surface of the heating resistor 6 serves as the reflective surface and the lower inner wall surface. Light reflected by the lower inner wall surface, which is the reflective surface, passes through the upper inner wall surface 4 and the observation surface 3. Thus, the state in the flow passage, that is, the state of the fluid, if there is any in the flow passage, can be optically observed.

It is sufficient that the upper inner wall surface 4 and the lower inner wall surface are respectively disposed at relatively upper and lower positions. These upper and lower positions are not limited to upper and lower positions in the direction of gravitational force. The reflective surface can be formed of the heating resistor 6 itself that actually produces heat, formed of at least one layer of a heat-conductive dielectric film disposed on the heating resistor 6, or formed of a metal film disposed on the heating resistor 6 and having a very low or very high resistance. A transparent insulating layer that functions as a reflection coating, or functions at least as a protective film, can be formed on the reflective surface of the heating resistor 6.

Electrically conductive members 7 and 8 function as electrodes and wiring for the heating resistor 6. With the electrodes and wiring, a current flows through part of or in the entirety of the heating resistor 6 to cause the heating resistor 6 to produce heat, thereby producing heat that heats the fluid in the flow passage 1. A circuit as an external power source can be connected to the electrically conductive members 7 and 8. A voltage from the circuit is applied between the electrically conductive members 7 and 8 so as to energize the heating resistor 6, thereby producing heat.

Referring to FIGS. 1B and 1C, a heating portion 9 is a portion that causes the temperature to rise, a non-heating reflective portion 10 is a portion that reflects light and does not produce heat, and a detection area 11 is an area the image of which is optically captured.

The heating resistor 6 is disposed at a position opposite the observation surface 3 so as to allow the state of the fluid in the flow passage 1 to be optically observed. Specifically, as illustrated in FIG. 1C or 1D, the heating resistor 6 can include the heating portion 9 and the non-heating reflective portions 10. The reflective portions 10 are not electrically connected to the heating resistor 6, which serves as the heating portion 9, and do not produce heat. In other words, with a structure in which part of a reflective member is the heating resistor 6, a reflecting function and a heating function are designed such that the reflecting and heating functions can be adjusted independently of each other.

In this case, as illustrated in FIG. 1C or 1D, gaps (slits 12) can be formed between the heating portion 9 and the non-heating reflective portions 10. The width of each slit 12 is preferably 50 µm or larger with respect to insulation between the heating portion 9 and the reflective portions 10, and preferably 1 mm or smaller with respect to detection resolution.

Alternatively, when at least two independent heating resistors 6 are provided in a direction in which the fluid flows in the flow passage 1, two independent real time processes can be simultaneously or successively performed.

The examples of the two processes to be performed can include a polymerase chain reaction (PCR) process such as a PCR process and a thermal melting process disclosed in PTL 1.

It is possible that a single flow passage 1 is used. Alternatively, a plurality of flow passages 1 parallel to one another can be disposed. With the plurality of flow passages 1, processing of a plurality of specimens or the like at a time is facilitated.

At least one of the metal reflective surface of the heating resistor 6 and the non-heating metal reflective portion 10 can have the transparent insulating layer formed thereon. The dielectric constant and the layer thickness of the insulating layer can also be adjusted so that the insulating layer functions as a reflection coating. The thickness of the insulating layer can be selected from a thickness in a range from 10 nm to 500 µm. The layer thickness is preferably n (here, n is an integer) times one fourth of the optical wave length λ of light to be detected. The transparent insulating layer can be formed of a metal compound such as silicon oxide, silicon oxynitride, aluminum oxide, or titanium oxide.

When light is emitted in the flow passage 1, light 13, which is directed toward the upper inner wall surface 4, and light 14, which is reflected by the reflective surface of the heating resistor 6, can be detected on the observation surface 3 side, thereby permitting highly sensitive detection. When fluorescent emission or another luminous phenomenon caused by illumination with excitation light is used as a detection signal, the length of an optical path is increased by reflection, thereby further increasing detection sensitivity.

The heating resistor 6 has a reflectivity which is significant in order not to allow light in the flow passage 1 to pass through the heating resistor 6 toward the second member 5, and in order to allow the light to be reflected toward the upper inner wall surface 4. The reflective surface of the heating resistor 6 can be a metal film, and in particular, a platinum film with respect to reflectivity and resistivity. The reflectivity of the metal film surface that serves as the reflective surface is preferably 80% or greater, more preferably 90% or greater, and even more preferably 95% or greater. A metal film having such reflectivity can be formed using a sputtering method in which a pressure, a substrate temperature, a substrate bias voltage, and so forth are adjusted. Alternatively, a smooth film having high reflectivity can be obtained by forming a metal film and then polishing the surface of the metal film. The material of the film having the reflective surface can be platinum, silver, aluminum, a platinum alloy, a silver alloy, an aluminum alloy, or the like. In the case where the reflective surface is formed of the heating resistor 6 itself, dimensions of the metal film, that is, the thickness of the film and the length and width of the pattern are set such that required heat can be obtained.

In the case where the heating resistor 6 is formed below a reflective film, the heating resistor 6 being electrically independent of the reflective film, the heating resistor 6 can be formed of a known resistance film made of such a material as titanium nitride, silicon nitride titanium, or hafnium boride, because consideration for reflectivity of the heating resistor 6 is dropped.

For the purpose of adjustment of the resistivity of the heating resistor 6, the thickness of the film of the heating resistor 6 can be varied in a direction in which the fluid flows in the flow passage 1. In the case where the heating resistor 6 has an elongated shape as illustrated in FIGS. 1A to 1D, heat capacities near longitudinal ends usually increase compared to that at a central portion. That is, when the heating resistor 6 is formed of a film of a single material, a temperature distribution in which the temperatures near the end portions of the heating resistor 6 are lower tends to occur. In order to suppress this, the film thickness and width on each end portion side are decreased compared to the central portion, thereby increasing the resistances of the end portions, and accordingly, facilitating production of heat at the end portions.

Side walls of the flow passage 1, which are walls of the flow passage 1 other than the upper inner wall surface 4 and the lower inner wall surface (that is, reflective surface) that opposes the upper inner wall surface 4 and is part of the heating resistor 6, can be either light transmissive or light reflective. In order to make the side surfaces light transmissive, it is sufficient that the first member 2 is formed of a light transmissive member and a depression is formed in the first member 2. In contrast, in order to make the side surfaces light reflective, it is sufficient that the second member 5 is formed of a non-light transmissive member and a depression is formed in the second member 5. Thus, the flow passage 1 can be formed by bonding two members (substrates) to each other. Alternatively, the flow passage device can be formed to have a three-layer structure having a gap member disposed between the two substrates.

Alternatively, the second member 5 can have, for example, a depression having a curved surface formed using isotropic etching, and the depression can be covered by a film having a reflective surface.

Testing System and Testing Method

Figure 2:
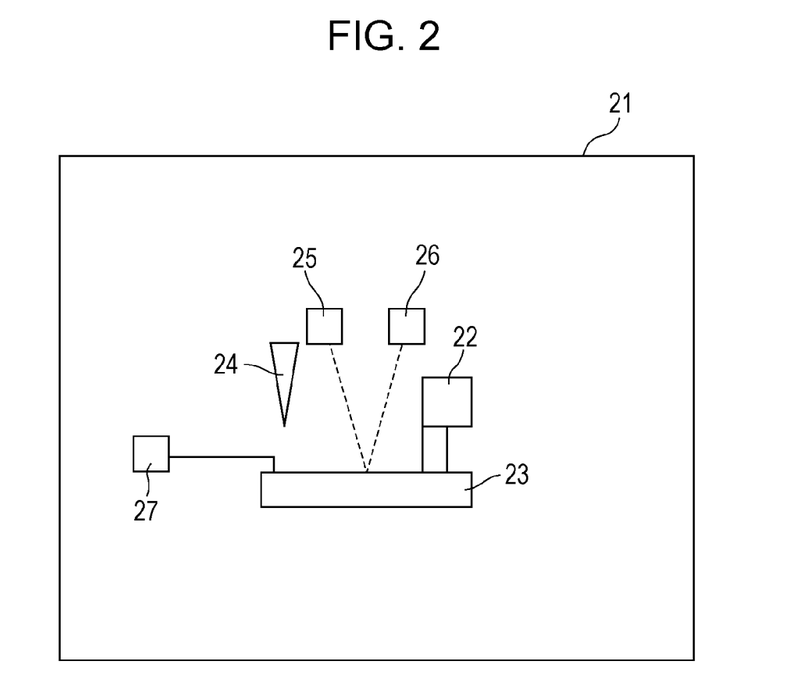
FIG. 2 is a schematic diagram illustrating a testing system according to the present invention.

The details of a testing system and a testing method using the above-described flow passage device will be described below with reference to FIG. 2.

A testing apparatus 21, which serves as the testing system, includes a receiving table (not shown), a light source, a light detector, and a circuit. The receiving table receives the above-described flow passage device, the light source emits light toward the flow passage device, the light detector detects light emitted in the flow passage device, and the circuit supplies a current to the heating resistor 6.

The testing apparatus 21 includes a pressure generator and a temperature measuring device according to need. The pressure generator causes a fluid to flow through the flow passage 1, and the temperature measuring device measures the temperature of the fluid in the flow passage 1 in accordance with the resistance of the heating resistor 6.

A pressure generator 22 is provided as a unit arranged to move a liquid in the flow passage 1 of a flow passage device 23. The pressure generator 22 generates a positive or negative pressure. The pressure generator 22 uses a pump such as a syringe pump that is connected to a discharge port of the flow passage device 23 to generate a pressure in the flow passage 1. Reference numeral 24 denotes a liquid introducing device such as a pipet.

A reaction detecting unit includes a light source 25 and a light detector 26, which are combined with each other. The light source 25, which serves as a light emitting unit, uses a laser, a light emitting diode (LED), or the like to illuminate the flow passage device 23, and the light detector 26 uses a charge-coupled device (CCD) image sensor, a complementary metal-oxide semiconductor (CMOS) image sensor, or the like. A circuit 27 is a power source which applies voltage to and energizes the heating resistor 6 through the electrically conductive members 7 and 8 of the flow passage device 23 so as to heat the interior of the flow passage 1. The testing apparatus 21 can includes therein a computer, which serves as a control unit that controls the above-described components.

As described later, the flow passage device 23 according to the present invention can be used as a single-chip fluorescence detection device having a PCR amplification area and a thermal analysis area. The PCR amplification area is equipped with the reflective heating resistor 6 on an upstream side of the flow passage 1 and the thermal analysis area is equipped with the other reflective heating resistor 6 on a downstream side of the flow passage 1.

The temperature measuring device, which is provided according to need, measures the temperature of the fluid in the flow passage 1 in accordance with a resistance of the heating resistor 6 calculated from the amperage of electricity flowing in the heating resistor 6 and a voltage applied to the heating resistor 6.

In the testing method according to the embodiment of the present invention, the above-described testing apparatus 21 and the flow passage device 23 are prepared, a fluid is supplied into the flow passage 1 of the flow passage device 23, the temperature of the fluid in the flow passage 1 is changed by heat produced by the heating resistor 6, thereby optically detecting the state of the fluid in the flow passage 1.

Figure 3:
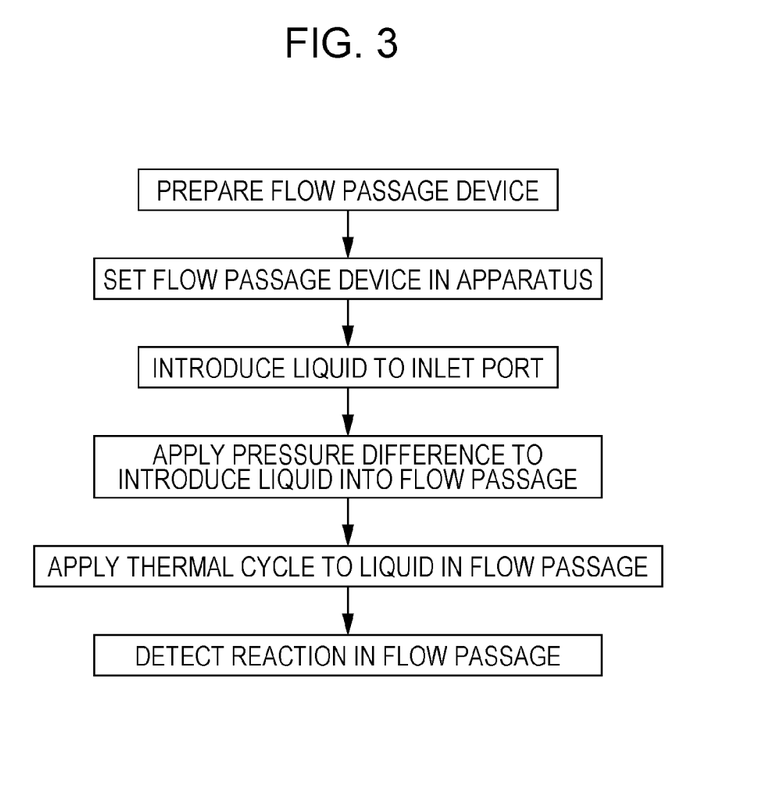
FIG. 3 is a flowchart of a testing method according to the present invention.

FIG. 3 is a flowchart of the testing method using the above-described testing apparatus 21. The above-described flow passage device 23 is initially prepared. Next, the flow passage device 23 is set in a receiving unit of the testing apparatus 21. Next, a liquid such as a reagent is introduced using a liquid introducing device 24 to an inlet port (an opening through which a liquid is supplied is normally provided) of the flow passage 1 of the flow passage device 23. After that, a pressure difference is applied into the flow passage 1 using the pressure generator 22, thereby introducing the liquid into the flow passage 1. Power is supplied from the circuit 27 to the heating resistor 6 of the flow passage device 23 to perform control by which the temperature of the liquid having been introduced into the flow passage 1 is changed. The temperature control includes, for example, application of a thermal cycle for PCR, in which the temperature is repeatedly increased and decreased, heating for measurement of thermal melting, and the like. Along with the temperature control, or after the temperature control has been performed, a reacting state of the liquid in the flow passage 1 is optically detected using the reaction detecting unit. As a result of the detection, the amount of the reaction (including the presence or absence of the reaction) can be determined, and accordingly, the reaction in the flow passage 1 can be analyzed.

Using the flow passage device 23 for light detection according to the present embodiment, in a detection through the upper inner wall surface 4 and the observation surface 3, light emitted in at least part of the flow passage 1 is detected along with light reflected by the reflective surface provided on the lower inner wall surface of the flow passage 1. In so doing, part or the entirety of the heating resistor 6 produces heat, thereby heating the fluid in the flow passage 1. This causes the temperature of the fluid to change. Since the above-described processes can be performed in a single flow passage 1, a highly sensitive analysis can be performed in a real time manner with respect to a temperature change. Thus, desirable testing can be performed.

The heating resistor 6 disposed on one of the wall surfaces of the flow passage 1 can be used as a temperature measuring device that measures temperature in the flow passage 1 in accordance with the resistance thereof. By feeding back this measurement result to the power source, heating temperature can be more precisely controlled.

Although in the present embodiment, two members, that is, the first member 2 and the second member 5, are bonded together to form the flow passage device 23, the flow passage device 23 is not limited to this. A third and fourth members can be disposed between the first and second members 2 and 5. Alternatively, the flow passage device 23 can be formed of a single member using photo-curable resin or the like.

The flow passage device 23 for light detection according to the present invention can be utilized as a medical testing device used in medical tests and diagnoses. The medical testing devices, a representative example of which are µ-TASs herein, generally refer to devices used in medical tests and diagnoses such as, for example, DNA chips, Labs-on-a-Chip, micro-arrays, and protein chips.

First Example

The present invention will be described in detail below with reference to examples.

Figure 4:
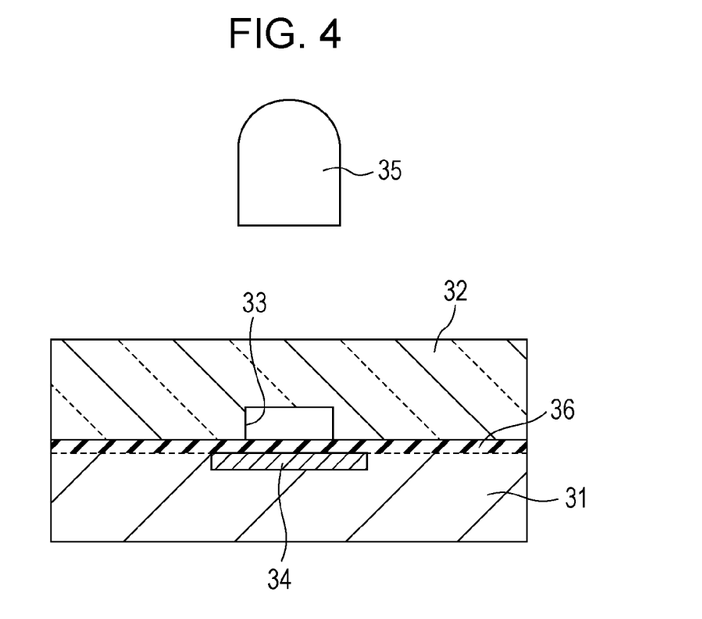
FIG. 4 is a sectional view illustrating a flow passage device according to a first example.

FIG. 4 is an explanatory diagram of the present example illustrating a section perpendicular to a flow passage. A second member 31 formed of a lower substrate, and a first member 32 is formed of a glass substrate. The present example also includes a flow passage 33, a plurality of heating resistors 34, a light detector 35, and an insulating layer 36. The lower substrate is formed of a single crystal Si. Single crystal Si is a material to which a variety of processing methods used in the micro electro mechanical system (MEMS) technology can be applied. Use of single crystal Si facilitates processing and control for processing a material into an intended shape. A metal pattern made of gold is formed on the lower substrate as electrically conductive members serving as wiring for the heating resistors 34. The insulating layer 36, which is transparent to wavelengths of light emitted in the flow passage 33, is formed on the metal pattern. The flow passage 33 is formed in the upper first member 32 by dry-etching. The first member 32 and the second member 31 can be integrated into a unit using a direct bonding method. Pads that have a certain size and used for electrical connection are provided at ends of the wiring. Through holes are formed in the first member 32 at positions corresponding to the pads so as to allow electrical connection to be routed therethrough. The light detector 35 is disposed above the first member 32 on a side opposite to the heating resistors 34 also serving as the reflective members. The light from the flow passage 33 passes through the first member 32 and reaches the light detector 35. In addition, the light from the flow passage 33 passes through the insulating layer 36, is reflected by the heating resistors 34, which also serve as the reflective members, and reaches the light detector 35.

According to the present example, control of the temperature of the flow passage 33 and detection of an optical signal can be simultaneously performed. In addition, since the heating resistors 34 function as heating units and reflective units, the flow passage device for light detection having a simpler structure can be realized.

In the present example, the heating resistors 34 disposed near the flow passage 33 function as heating portions. The flow passage 33 and the heating resistors 34 are disposed with the insulating layer 36 interposed therebetween. Thus, the plurality of heating resistors 34 are not electrically connected to one another through a liquid flowing in the common flow passage 33. As is the case with the embodiment illustrated in FIG. 1B or 1C, the metal pattern of the heating portions of the heating resistors 34 can be a pattern, of which the size is equal to or less than a size corresponds to the resolution of an image sensor serving as the light detector 35.

Second Example

Figure 5:
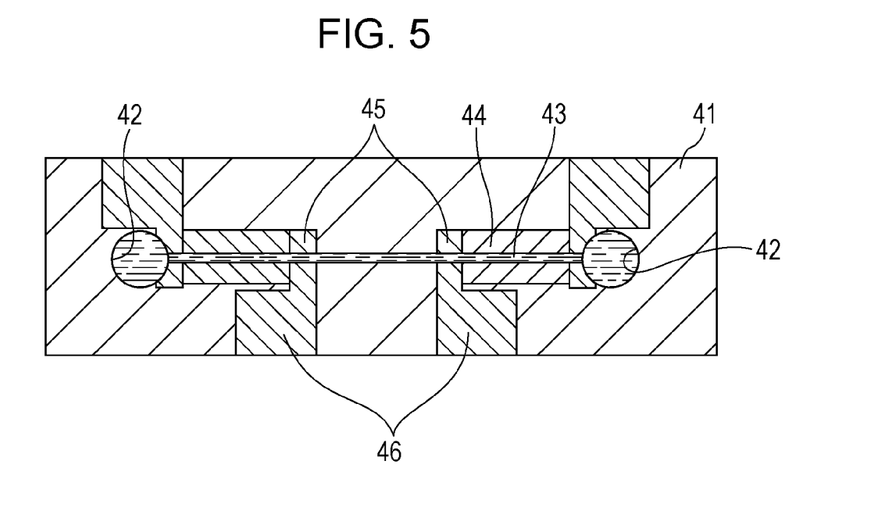
FIG. 5 is a diagram illustrating a flow passage device according to a second example.

FIG. 5 is a schematic diagram of a flow passage device seen from above. The flow passage device includes a substrate 41, inlet/outlet ports 42 through which a viscous fluid flows into or out of a flow passage, a flow passage 43, heating resistors 44 as heating portions, wiring 45, electrode pads 46, a light detector (not shown), and a transparent insulating layer (not shown).

The present example includes two heating resistors 44 along the flow passage 43. There has been proposed a method of DNA or RNA testing in which amplification using the PCR reaction having been mentioned above is performed and combination with a single-strand, which is labeled with fluorescent dye, or separation from a double-strand, which is labeled with fluorescent dye, is observed. In the present example, an area in which one of the heating resistors 44 is disposed is used as a PCR reaction area, and an area in which the other heating resistor 44 is disposed is used as an analytical area in which a thermal analysis is performed. When a plurality of independent heating portions are provided for temperature adjustment areas as described above, amplification and analysis can be continuously performed without being interfered with each other.

In addition to use of fluorescence detection in DNA testing, dye that emits light due to chemical reaction is used in processes in which a liquid is transported during, before or after the PCR amplification. This allows the position of a liquid to be monitored. Thus, the state of liquid transportation can be controlled. Also in this case, a desirable optical signal can be obtained using the heating portions that also serve as reflective units.

Third Example

Figure 6:
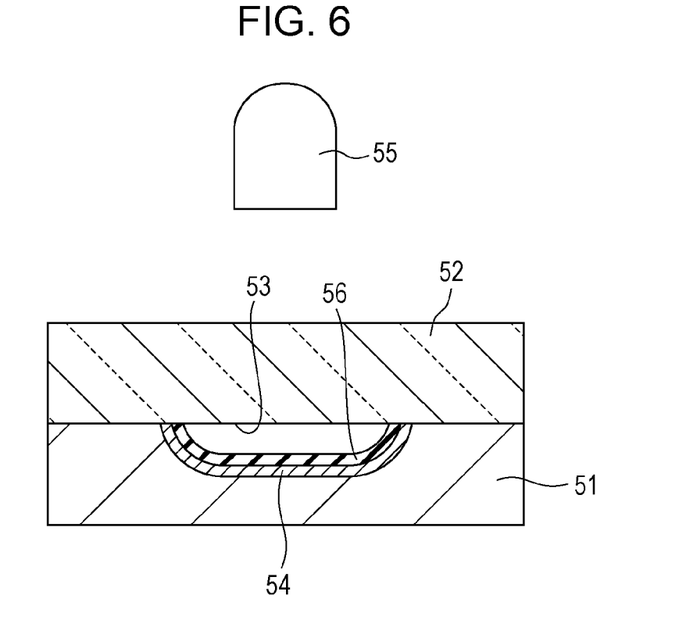
FIG. 6 is a sectional view illustrating a flow passage device according to a third example.

FIG. 6 illustrates a section perpendicular to a flow passage. The present example includes a lower substrate 51, an upper substrate 52, a flow passage 53, a heating resistor 54 as the heating portion, a light detector 55, and an insulating layer 56.

The flow passage 53 is formed in the lower substrate 51. A surface of the flow passage 53 has a continuously curved sectional shape formed by isotropic wet etching. A metal pattern which serves as the heating portion is formed on the flow passage 53. Grooves having depths equal to the film thickness of wiring for the heating portion is formed in the lower substrate 51. The wiring for the heating portion is routed along the grooves. As is the case with the first example, the third example has the insulating layer 56. The upper substrate 52 formed of glass is integrated with the lower substrate 51 using anode bonding so as to overlay the flow passage 53. Pads that have a certain size and used for electrical connection are provided at ends of the wiring. Through holes are formed in the upper substrate 52 so as to allow electrical connection to be routed therethrough.

In the present example, isotropic etching is performed on the lower substrate 51 so as to obtain inner wall of the flow passage 53, of which, in a sectional view, side portions are connected to a bottom portion with curves so as to continuous with the bottom portion. By forming a heating element in the inner wall, fractures of a film do not occur during formation of the film, thereby desirably forming the film serving as the heating resistor 54. In addition, with respect to reflection of light emitted in the flow passage 53, since the reflective surface is directed to the light detector 55, a desirable optical signal can be obtained.

Fourth Example

Figure 7:
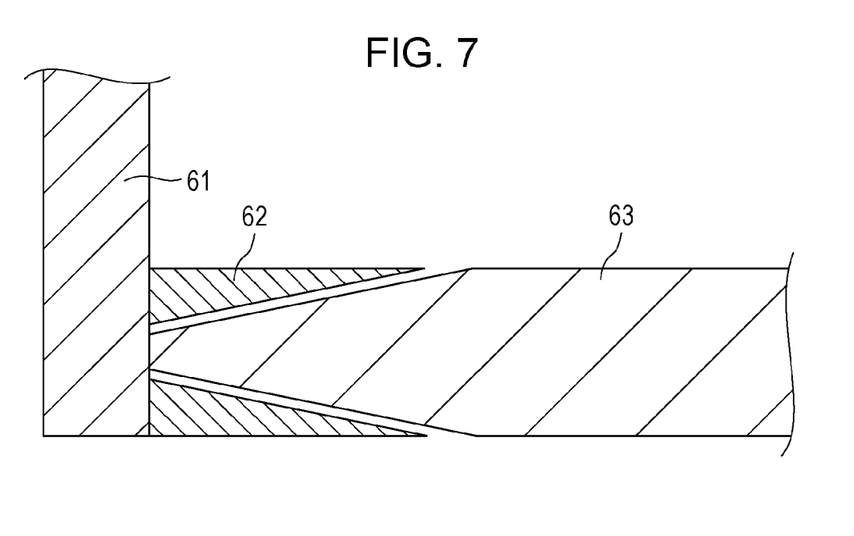
FIG. 7 is a diagram illustrating a flow passage device according to a fourth example.

FIG. 7 is an enlarged view of a heating portion and wiring, in particular a connecting portion. In FIG. 7, reference numeral 63 denotes the heating portion, reference numeral 61 denotes wiring, and reference numeral 62 denotes an additional pattern serving as non-heating portions. There can be made to be a distribution of effective resistance values by varying the pattern of the heating portion 63. A temperature distribution tends to occur at ends of the heating portion 63 (heating portion) in particular. Thus, increasing the amount of heat production at the ends of the heating portion is effective.

However, a decrease in the width of the heating portion pattern means a decrease in a reflective area. For this reason, in the present example, slits are formed in the heating portion pattern. Each slit has a size equal to or smaller than the resolution limit of an imaging system of a light detecting unit. A size equal to or smaller than a resolution limit ideally refers to a size which is not recognizable by an imaging optical system and an observation device used due to their performances. However, in the present example, a signal is averaged in a flow passage width direction and observed, and, even when an image is not completely resolved, the effect on the averaged signal is limited to 10% or less of the strength of the signal in the design. As a result, the reflective member can be separated into the heating portion 63 and the non-heating portions 62 (additional patterns). The heating portion 63 functions as heating resistor. Although the non-heating portions 62 are electrically connected, each non-heating portion 62 does not have a path for a current to flow, and accordingly, does not produce heat. Nowadays, the micro-fabrication is used to process a material at very small dimensions. Thus, electrical isolation that is not detected by a detecting unit can be realized. Thus, a heating temperature distribution can be easily realized using a structure similar to that of the first example. By setting the size of each slit to be equal to or smaller than the resolution limit, a reflectivity distribution and a temperature distribution can be independently set.

Fifth Example

In another example, the width of the heating portion is maintained while the thickness of the heating portion decreases toward the end portions of the heating portion. Also in the present example, resistance per unit length can be distributed, and accordingly, heat production can be distributed. When the heating portion is observed from an image sensor as an observation unit, the pattern has a constant width and a reflecting area is not changed. Also in the present example, a reflectivity distribution and a heating temperature distribution can be independently adjusted.

Sixth Example

Figure 8:
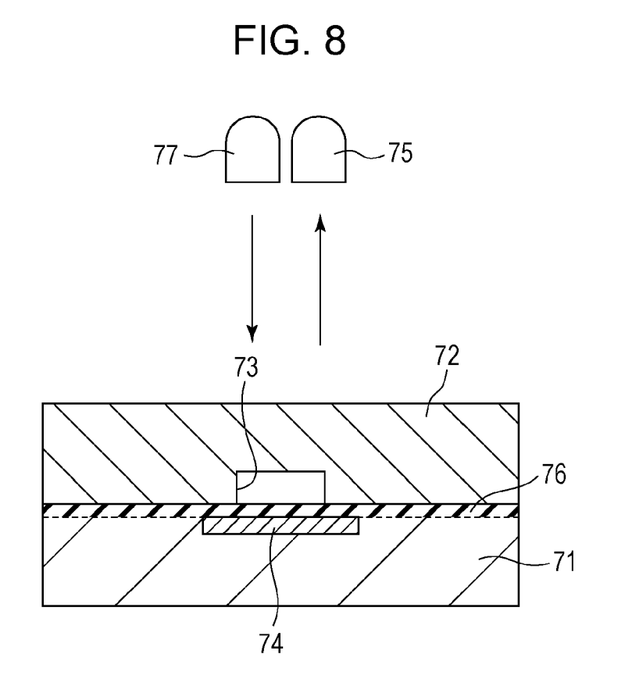
FIG. 8 is a sectional view illustrating a flow passage device according to a sixth example.

FIG. 8 is an explanatory diagram of the present example illustrating a section perpendicular to a flow passage in a flow passage device for light detection. The present example includes a lower substrate 71, an upper substrate 72, a flow passage 73, a heating resistor 74, a light detector 75, an insulating layer 76, and a light source 77. The heating resistor 74 also serves as the reflective member.

A fluid flowing in the flow passage 73 has the absorption ratio with respect to the wavelength of light from the light source 77, the absorption ratio changing in accordance with reaction. The light emitted from the light source 77 is transmitted through the flow passage 73, reflected by a reflective surface of the heating resistor 74, and observed by the light detector 75. Also in the present example, desirable optical detection can be performed while the temperature of the flow passage 73 is changed by the heating portion.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-105635, filed May 10, 2011, which is hereby incorporated by reference herein in its entirety.

REFERENCE SIGNS LIST

1 flow passage
2 first member
3 observation surface
4 upper inner wall surface
5 second member
6 heating resistor
7, 8 electrically conductive member
9 heating portion
11 detection area

The invention claimed is:

1. A flow passage device having a flow passage, wherein the flow passage device is able to heat a fluid in the flow passage, and wherein a state of the fluid in the flow passage is observable using light, the flow passage device comprising:
   an observation surface used for observing a state in the flow passage;
   a first inner wall surface that is part of inner walls of the flow passage; and
   a second inner wall surface that opposes the first inner wall surface and that is part of the inner walls of the flow passage,
   wherein a heating resistor is provided in the second inner wall surface, wherein the heating resistor has a reflective surface that reflects light, and
   wherein the second inner wall surface is, aside from the heating resistor, provided with a reflective member that does not produce heat, wherein the reflective member is provided adjacent to the heating resistor with a gap therebetween.

2. The flow passage device according to claim 1, wherein the heating resistor has an elongated shape and the reflective member that does not produce heat is provided next to each long side of the heating resistor in such a manner that the reflective member is adjacent to the heating resistor with a gap therebetween.

3. The flow passage device according to claim 1, wherein the gap is 50 μm or more and 1 mm or less.

4. The flow passage device according to claim 1,
wherein a plurality of flow passages are provided, and
wherein each of the plurality of flow passages is disposed parallel to one another.

5. The flow passage device according to claim 1,
wherein the heating resistor or each of at least two heating resistors has a transparent insulating layer on the reflective surface thereof, and
wherein the transparent insulating layer serves as a reflection coating.

6. The flow passage device according to claim 1,
wherein the reflective surface or each of reflective surfaces is formed of a metal film, and
wherein the metal film includes portions of different thicknesses that are located upstream and downstream with respect to the direction in which the fluid flows in the flow passage or in each of a plurality of flow passages.

7. A testing system comprising:
a receiving table that receives the flow passage device according to claim 1;
a light source that emits light toward the flow passage device;
a light detector that detects light from the flow passage device; and
a circuit that supplies a current to the heating resistor or each of at least two heating resistors.

8. The testing system according to claim 7, further comprising:
a pressure generator that causes the fluid to flow in the flow passage or each of a plurality of flow passages; and
a temperature measuring device that measures a temperature of the fluid in the flow passage or each of the plurality of flow passages in accordance with a resistance of the heating resistor or resistances of the at least two heating resistors.

9. A method of testing a fluid, the method comprising:
preparing the flow passage device according to claim 1;
supplying the fluid to the flow passage or to at least one of a plurality of flow passages;
causing the heating resistor or at least one of at least two heating resistors to produce heat to change a temperature of the fluid in the flow passage or in the at least one of the plurality of flow passages; and
detecting an optical state of the fluid in the flow passage or in the at least one of the plurality of flow passages.

10. The method of testing according to claim 9, the method further comprising measuring a temperature of the fluid in the flow passage or in the at least one of the plurality of flow passages in accordance with resistance of the heating resistor having been heated or at the least one of the at least two heating resistors having been heated.

11. A flow passage device having a flow passage, wherein the flow passage device is able to heat a fluid in the flow passage, and wherein a state of the fluid in the flow passage is observable using light, the flow passage device comprising:
a first member that includes
an observation surface used for observing a state in the flow passage, and
an upper inner wall surface that is part of inner walls of the flow passage; and
a second member that includes
a lower inner wall surface that opposes the upper inner wall surface and that is part of the inner walls of the flow passage,
wherein a heating resistor is provided in the lower inner wall surface of the second member, wherein the heating resistor has a reflective surface that reflects light,
wherein the light reflected by the reflective surface passes through the upper inner wall surface and the observation surface, and
wherein the lower inner wall surface is, aside from the heating resistor, provided with a reflective member that does not produce heat, wherein the reflective member is provided adjacent to the heating resistor with a gap therebetween.

12. The flow passage device according to claim 11,
wherein the second member has a depression having a curved surface formed using isotropic etching, and
wherein the depression is covered by a film having the reflective surface.

* * * * *